(12) United States Patent
Brueck et al.

(10) Patent No.: US 11,474,094 B2
(45) Date of Patent: Oct. 18, 2022

(54) INNOVATIVE NANOPORE SEQUENCING TECHNOLOGY

(71) Applicant: UNM RAINFOREST INNOVATIONS, Albuquerque, NM (US)

(72) Inventors: Steven R. J. Brueck, Albuquerque, NM (US); Jeremy Scott Edwards, Albuquerque, NM (US); Alexander Neumann, Albuquerque, NM (US); Yuliya Kuznetsova, Albuquerque, NM (US); Edgar A. Mendoza, Albuquerque, NM (US)

(*) Notice: Subject to any disclaimer, the term of this patent is extended or adjusted under 35 U.S.C. 154(b) by 397 days.

(21) Appl. No.: 16/215,139

(22) Filed: Dec. 10, 2018

(65) Prior Publication Data
US 2019/0227050 A1     Jul. 25, 2019

Related U.S. Application Data

(63) Continuation of application No. 15/039,825, filed as application No. PCT/US2014/067764 on Nov. 26, 2014, now Pat. No. 10,184,930.
(Continued)

(51) Int. Cl.
*G01N 33/487* (2006.01)
*C12Q 1/6869* (2018.01)
(Continued)

(52) U.S. Cl.
CPC .. *G01N 33/48721* (2013.01); *B01L 3/502707* (2013.01); *B01L 3/502761* (2013.01);
(Continued)

(58) Field of Classification Search
CPC .............. G01N 3/48721; G01N 21/65; G01N 2021/653; G01N 2201/061;
(Continued)

(56) References Cited

U.S. PATENT DOCUMENTS

2002/0197618 A1* 12/2002 Sampson ............. C12Q 1/6806
                                                        435/6.12
2003/0187237 A1    10/2003 Chan et al.
(Continued)

FOREIGN PATENT DOCUMENTS

| CN | 101842692 A | 9/2010 |
|---|---|---|
| CN | 102753708 A | 10/2012 |
| WO | 2009030953 A1 | 3/2009 |

OTHER PUBLICATIONS

Chen, Zhu, et al. "DNA Translocation through an Array of Kinked Nanopores." Nature Materials, vol. 9, No. 8, 2010, pp. 667-675., doi:10.1038/nmat2805. (Year: 2010).*
(Continued)

*Primary Examiner* — Bethany L Martin
*Assistant Examiner* — Kourtney R S Carlson
(74) *Attorney, Agent, or Firm* — MH2 Technology Law Group LLP

(57) ABSTRACT

Methods and apparatus for long read, label-free, optical nanopore long chain molecule sequencing. In general, the present disclosure describes a novel sequencing technology based on the integration of nanochannels to deliver single long-chain molecules with widely spaced (>wavelength), ~1-nm aperture "tortuous" nanopores that slow translocation sufficiently to provide massively parallel, single base resolution using optical techniques. A novel, directed self-assembly nanofabrication scheme using simple colloidal nanoparticles is used to form the nanopore arrays atop nanochannels that unfold the long chain molecules. At the surface of the nanoparticle array, strongly localized electromagnetic fields in engineered plasmonic/polaritonic structures allow for single base resolution using optical techniques.

16 Claims, 8 Drawing Sheets

Related U.S. Application Data

(60) Provisional application No. 61/909,116, filed on Nov. 26, 2013.

(51) Int. Cl.
| | |
|---|---|
| *G01N 21/65* | (2006.01) |
| *B01L 3/00* | (2006.01) |
| *C23C 16/34* | (2006.01) |
| *C23C 16/455* | (2006.01) |
| *C23C 16/50* | (2006.01) |

(52) U.S. Cl.
CPC .......... *C12Q 1/6869* (2013.01); *C23C 16/345* (2013.01); *C23C 16/45525* (2013.01); *C23C 16/50* (2013.01); *G01N 21/65* (2013.01); *B01L 2200/0663* (2013.01); *B01L 2200/0689* (2013.01); *B01L 2200/12* (2013.01); *B01L 2300/046* (2013.01); *B01L 2300/0654* (2013.01); *B01L 2300/087* (2013.01); *B01L 2300/0816* (2013.01); *B01L 2300/0896* (2013.01); *B01L 2300/16* (2013.01); *B01L 2300/168* (2013.01); *B01L 2400/0421* (2013.01); *G01N 2021/653* (2013.01); *G01N 2201/061* (2013.01)

(58) Field of Classification Search
CPC ......... B01L 3/502707; B01L 3/502761; B01L 2200/0663; B01L 2200/0689; B01L 2200/12; B01L 2300/046; B01L 2300/0654; B01L 2300/0816; B01L 2300/087; B01L 2300/0896; B01L 2400/0421

See application file for complete search history.

(56) References Cited

U.S. PATENT DOCUMENTS

| | | | |
|---|---|---|---|
| 2005/0084980 A1* | 4/2005 | Koo | G01J 3/44 436/171 |
| 2006/0275911 A1 | 12/2006 | Wang et al. | |
| 2008/0041733 A1* | 2/2008 | Hibbs | C12Q 1/6869 205/775 |
| 2011/0011794 A1* | 1/2011 | Brueck | B82Y 30/00 210/500.23 |
| 2011/0036994 A1 | 2/2011 | Frayling | |
| 2011/0212512 A1 | 9/2011 | Wang et al. | |
| 2011/0236984 A1 | 9/2011 | Sun et al. | |
| 2012/0160687 A1* | 6/2012 | Akeson | C12Q 1/6869 204/540 |
| 2013/0176563 A1* | 7/2013 | Ozawa | G01N 21/658 356/301 |
| 2013/0193065 A1* | 8/2013 | Brueck | G03F 7/2051 210/500.23 |
| 2013/0270521 A1* | 10/2013 | Peng | G01N 33/48721 257/29 |

OTHER PUBLICATIONS

Chang Chen, et al. "Detection of DNA Bases and Oligonucleotides in Plasmonic Nanoslits Using Fluidic Sers." IEEE Journal of Selected Topics in Quantum Electronics, vol. 19, No. 3, 2013, pp. 4600707-4600707., https://doi.org/10.1109/jstqe.2012.2226564. (Year: 2013).*
SIPO, "First Office Action," English translation of First Office Action dated Jun. 12, 2017, 4 pages.
SIPO, "Search Report," English translation of Search Report issued with First Office Action dated Jun. 12, 2017, 2 pages.
Extended European Search Report dated Jun. 14, 2017, European Application No. 14865949.3, pp. 1-8.
Zhu Chen et al., "DNA translocation through an array of kinked nanopores", Nature Materials, vol. 9, Aug. 2010, pp. 667-675.
Dukhyun Choi et al., "Self-Organized Hexagonal-Nanopore SERS Array", Small, vol. 6, No. 16, Jul. 2010, pp. 1741-1744.
International Search Report and Written Report dated May 27, 2015 from International Application No. PCT/US2014/067764, pp. 1-14.
Nam et al., "Sub-10-nm Nanochannels by Self-Sealing and Self-Limiting Atomic Layer Deposition," American Chemical Society, Nano Letters 2010, 10, 3324-3329.

* cited by examiner

INNOVATIVE NANOPORE SEQUENCING TECHNOLOGY

CROSS REFERENCE TO RELATED APPLICATIONS

This application is a continuation and claims benefit of priority U.S. patent application Ser. No. 15/039,825 filed on Mary 26, 2016, which is a U.S. National Stage Application of PCT/US2014/067764 filed on Nov. 26, 2014, which claims the benefit of U.S. Provisional Application Ser. No. 61/909,116 filed on Nov. 26, 2013, which are incorporated by reference herein in their entireties.

BACKGROUND

The human genome is diploid, and a genome sequence is not complete unless all polymorphisms or variants are phased and assigned to specific chromosomes. Additionally, the entire chromosome landscape must be decoded, including complex structural variants in the genome (i.e., aneuploidy, translocations, inversions, duplications, loss of heterozygosity, etc). For example, balanced translocations occur in approximately 1 in 500 individuals, trisomy 21 occurs in as many as 1 in 650 live births, and extensive genome instability occurs in many cancers. Accordingly, complete genome sequencing must be able to identify all complex genome variants.

There are a number of ultra-high-throughput sequencing technologies available (e.g., Illumina/Solex, SOLiD, Roche/454, PacBio, Ion Torrent, etc.) and under development [e.g., ZS Genetics, IBM GE (U.S. Pat. No. 7,264,934), Oxford Nanopore, Noblegen, Bionanomatrix, and GnuBIO. While the cost of sequencing has decreased dramatically, the technology is still unable to completely sequence a human genome. There remain numerous regions of the human genome that are still not sequenced in the GRCh37 version of the genome, which consists of 249 scaffolds (http://www.ncbi.nlm.nih.gov/projects/genome/assembly/grc/data.shtml). Additionally, all current commercial technologies require a reference genome for a high quality assembly. While de novo genome assemblies are possible with short read technologies, the quality is low relative to resequencing projects. These problems limit the ability of next generation sequencing platforms to identify certain variants, such as large structural changes and repeated regions.

High throughput, long-read sequencing technologies are essential for resolving the complexities of the human genome. The human genome is diploid, meaning there are two copies each of 22 autosomes and two copies of the sex chromosomes (XX or XY). Long reads are essential to phase the genetic variants that are unique to each of the homologous chromosomes. Additionally, repetitive regions in the genome make sequencing impossible with short reads.

Recent advances in next generation sequencing technologies, along with the development of robust analytical methods, have given researchers the ability to determine the role of sequence variations in a variety of human diseases. However, the vast majority of these approaches produce results that are limited to finding polymorphisms while neglecting the importance of haplotypes. Today the most commonly studied variations are single-nucleotide polymorphisms (SNPs) and small insertions and deletions (InDels). This is because current generation sequencing methods, while proficient in identifying heterozygous loci, are unable to assign polymorphisms to one of the two homologous chromosomes, thus complicating the search for gene/disease associations. The HapMap and other projects are developing a haplotype map, but new approaches are required to address the cis and trans relationships in variants that occur in rare genotypes (e.g., novel somatic mutations) or in altered genomes (e.g., cancer).

The lack of haplotype information obtained from current sequencing approaches limits scientists' ability to draw important biological and medical conclusions, namely, because lists of polymorphisms are classified as homozygous or heterozygous, they neglect the importance of the context of each polymorphism. As a consequence, researchers often focus only on the variants that occur in protein coding regions (the exome), since only their importance can be predicted. Without the context of knowing whether variants in intergenic regions are linked in cis and/or through long-range chromatin interactions to affected genes, it is not possible to predict whether such variants are detrimental. The principal advantage of haplotype resolved sequencing over standard whole genome sequencing (WGS) is that all polymorphisms are assigned to a specific chromosome (e.g., maternal vs. paternal), and links are established between mutations (or variants) in distant regulatory elements and cis-linked genes on the same chromosome.

The limitations associated with direct haplotype sequencing primarily revolve around the relatively short read-length and 'phase insensitivity' of the current platforms. There have been a few approaches to generate haplotype resolved sequence, but these are not consistent with the $1,000 genome goal, due to the complexity and additional cost associated with the processes upstream of sequencing.

Nanopore DNA sequencing technologies are attractive since they offer direct access to the DNA sequence information without amplification or complex post processing of the sequence information, and hold the promise of long reads at high speed. There is a long history of research and development in various nanopore technologies. However, the promise has yet to be fully realized, and—in fact—no reads other than of specially constructed test DNA samples have been reported. (check with Jeremy on this statement) Additionally, single base resolution has not been reported with nanopore technologies. The issues identified in previous research include:

1. Transduction speed of ~1 base/µs (requiring high bandwidth electrical detection with concomitant noise and statistical fluctuation issues).
2. Longitudinal resolution greater than single base (typically ~4 bases for biological pores)[35].
3. Massively parallel application is difficult with electrical readout mechanisms.

Both biological and solid-state nanopore technologies have been investigated. For biological systems α-haemolysin and genetically-engineered MspA are the most common nanopores, and various techniques to slow the DNA translocation have been demonstrated, involving the use of enzymes or modification of the ssDNA strand to be interrogated with regions of dsDNA or other disturbances to slow the translocation. However, the difficulty associated with the large number of bases within the nanopore remains.

For solid-state pores the most common materials are silicon nitride and sapphire using ion- or electron-beam technologies to form the nanoscale pores. Graphene is another material that is attracting much attention. Atomic layer deposition can be used post-lithography to refine the pore dimensions. Hybrid technologies, adding biological structures to solid-state pores have also been investigated. Notwithstanding all of this activity, the promise of nanopore technology has yet to be achieved.

One final issue with all of these approaches is the need to scale to massively parallel applications with cost-effective fabrication. Present fabrication approaches are dominated by direct-write technologies (electron-beam and ion-beam lithographies), which are not scalable to massively parallel architectures, nor compatible with widespread adoption of the technology at low cost. Electrical measurements are not easily scaled to parallel measurements in an ionic fluid environment, optical measurements provide the most promising route to parallelism—the issue is providing the necessary single base resolution.

SUMMARY

The present disclosure provides methods and apparatus for long read, label-free, optical nanopore long chain molecule sequencing. In general, the present disclosure describes a novel sequencing technology based on the integration of nanochannels to deliver single long-chain molecules with widely spaced (>wavelength), ~1-nm aperture "tortuous" nanopores that slow translocation sufficiently to provide massively parallel, single base resolution using optical techniques. A novel, directed self-assembly nanofabrication scheme using simple colloidal nanoparticles is used to form the nanopore arrays atop nanochannels that unfold the long chain molecules. At the surface of the nanoparticle array, strongly localized electromagnetic fields in engineered plasmonic/polaritonic structures allow for single base resolution using optical techniques. Surface Enhanced Coherent Anti-Stokes Raman Spectroscopy (SE-CARS) is one such technique that has the advantage of not requiring labeling of the bases. Fluorescence techniques with labeled bases provides an alternative possibility.

DETAILED DESCRIPTION

Figure 1:
FIG. 1 is a schematic illustration of an exemplary method of nanochannel fabrication.

According to a first embodiment, the present disclosure provides a nanochannel including a system of tortuous nanopores having a partially sealed porous roof. According to another embodiment, the nanochannel further comprises an integrated metal-insulator-metal (MIM) plasmonic or plaritonic structure that enhances optical detection of detectable elements within a sample and provides the necessary spatial localization. According to yet another embodiment the present disclosure provides methods and apparatus for long read, label-free, optical nanopore long chain molecule sequencing. Suitable long chain molecules (sometimes referred to herein as "molecules" or "molecules of interest") include DNA, RNA, proteins, etc. Of course it will be understood that while various embodiments and examples may make reference to a specific type of long chain molecule, such as DNA, unless otherwise specifically stated, the present disclosure contemplates that such embodiments and examples are similarly applicable to other types of long-chain molecules including, but not necessarily limited to RNA and proteins.

According to some embodiments, the sequencing technology described herein may be capable of sequencing a full human genome in under one day for a cost of ~$100. According to various embodiments, the technology described herein make use of one or more of: an integrated system of nanochannels; tortuous (extended and convoluted) nanopores at a separation greater than an optical wavelength; a metal-insulator-metal (MIM) plasmonic or polaritonic structure, or other optical detection enhancement structure as described herein; and an optical readout mechanism such as surface-enhanced coherent anti-Stokes Raman scattering or labeled fluorescence techniques.

According to still further embodiments, the present disclosure provides methods for making each of the above. According to some embodiments, only a single, straightforward lithography step, at an easily accessed pitch of ~1 μm is required. According to various embodiments, nanoscale features are produced by directed self-assembly processes making this an inexpensive and field-replaceable technology.

According to various embodiments, the present disclosure utilizes nanochannels formed from nanoparticles. According to an embodiment, self-assembled nanochannels can be formed by directed spin-coating of nanoparticles (~50 nm diameter or less) onto photoresist walls, formed by a sequence of lithography steps that include some appropriate variant of exposure, development and etching as is well known in the art, such that the nanoparticles are "stacked up" to form the nanochannel walls and roofs. Suitable materials for forming the nanoparticles include materials for which a method to remove the photoresist exists. Furthermore, it will be understood that in those embodiments wherein the nanochannel is to be used with nucleic acids, the material should be hydrophillic to enable filling of the nanopores with a solution and negatively charged to enable translocation of the nucleic acids through the nanopores. According to a specific embodiment, silica nanoparticles have been found to meet all of the above-identified requirements. The spin-coating step is followed by a "lost-wax" calcination step that burns out the photoresist, sinters the nanoparticles to provide mechanical strength, and provides a hydrophilic surface for fluid introduction. Alternate processes such as solvent removal can be used to remove the photoresist and the ARC layers. Additional details for the formation of such nanochannels can be found in U.S. Pat. No. 7,825,037, which is hereby incorporated by reference.

Figure 2:
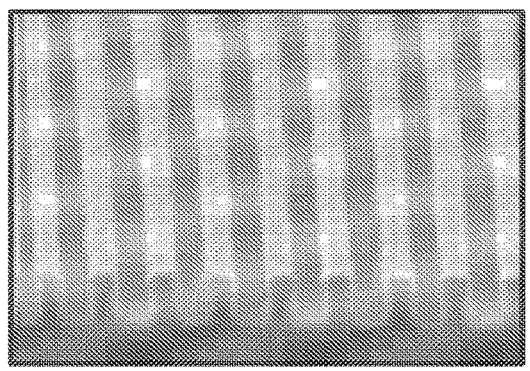
FIG. 2 is an SEM image showing a photoresist pattern for forming nanochannels having a 1 µm pitch.

Turning now to FIG. 1, which is a schematic illustration of an exemplary method of nanochannel fabrication, it can be seen that in the depicted embodiment, nanochannel fabrication includes multiple steps. First, a substrate (for example, quartz or fused silica) is spin-coated with a bottom antireflection coating and then a photoresist layer. Next, lithography is performed on the photoresist layer to define the nanochannels with a spacing that is larger than the optical resolution of the readout system (See, e.g., FIG. 2). For example, a period of ~1 μm and a linewidth of 10- to 100-nm might be used. However, it will be appreciated that both smaller and larger periods and linewidths are readily available. According to the embodiment shown in FIG. 2, interferometric lithography can be used to form the nanochannels, and these dimensions are well within the capabilities of even one or two generation old lithographic tools, offering a ready extension to volume manufacturing. Next, the antireflection layer is etched to expose the substrate. Colloidal nanoparticles (for example, silica nanoparticles) are then spin-coated on the photoresist pattern, thus depositing them in a layer-by-layer fashion first in the spaces between the photoresist lines to form the nanochannel sidewalls and finally extending over the photoresist to form the nanochannel roofs.

Figure 3:
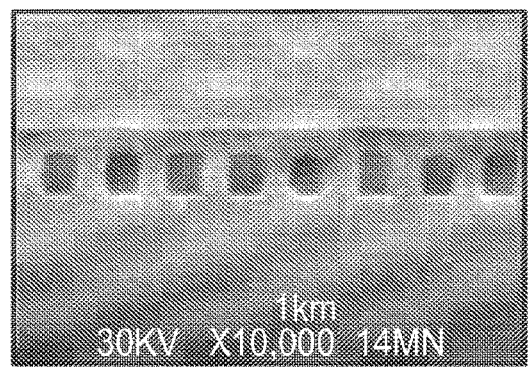
FIG. 3 is an SEM image showing 1D enclosed channels formed using the techniques described herein.
Figure 4:
FIG. 4 is an SEM image of 500 nm wide channel walls formed by 50-nm diameter silica nanoparticles.
Figure 5:
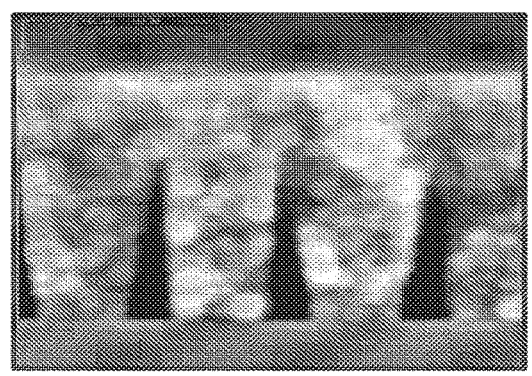
FIG. 5 is an SEM image of 100 nm wide channels formed using the techniques described herein.

As easily seen in FIGS. 3-5, the nanoparticles form both the sidewalls and the roofs of the nanochannels, with the nanoparticles in the roof forming tortuous nanopores, which, should a sample be placed in the nanochannels, the DNA molecules would have to traverse the pores in order to reach the roof and vice versa. According to some embodiments, 50-nm-diameter silica nanoparticles are used, but both the size and the material structure are flexible. Capillary forces during deposition force the nanoparticles (NP) into a hexagonal close-packed geometry. As a rough estimate, this means that the spaces between nanoparticles are ~NP diameter/3 or ~17 nm. The pores are complex, 3D paths, similar to the spacings and open paths created when oranges are piled up in the local supermarket. However, it should be understood that the actual structure is highly complex due to the significant dispersion in nanoparticle sizes which is under the control of the nanochannel fabricator. For the purposes of the present disclosure, we refer to the spacings and open paths created by the nanoparticles as "tortuous nanopores." In layer-by-layer deposition, steric effects due to the NP size dispersion will create a range of nanopore sizes.

After spin-coating of the nanoparticles, the structure is then calcined (~800° C. in an air ambient) to remove the remaining hydrocarbon films, to sinter the nanoparticles for additional mechanical strength, and to prepare the nanoparticles in a hydrophilic state that allows simple capillary filling of the nanochannels with buffer/sample solution.

Figure 6:
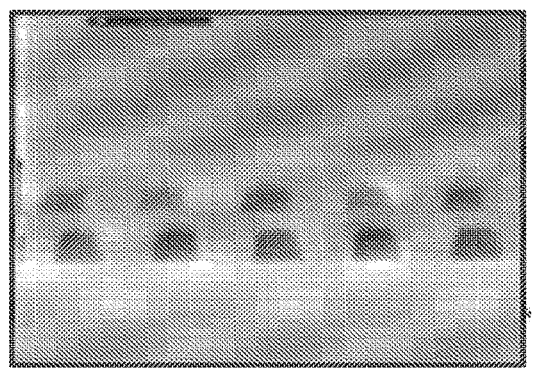
FIG. 6 is an SEM image showing a multi-layered nanochannel formed using the techniques described herein.

It will be readily understood that this is a very flexible nanochannel fabrication process. For silica nanoparticles, a simple dry etch step allows for reservoirs with access to entry ports of the nanochannels and to provide electrodes for electrophoretic transport and stretching. An additional feature is the ability to stack several nanochannels with either parallel or perpendicular nanochannel directions, simply by repeating the above-process. See, e.g., FIG. 6, which shows stacked nanochannels. In addition to the nanochannel structure it is often desirable to introduce a secondary roof spaced away from the nanochannel roof. This ensures a flat surface for the buffer solution that moves from the nanochannels to the roof, provides a channel for flowing the target molecules away from the pore and allows an additional electrode for controlling the translocation velocity.

Figure 7:
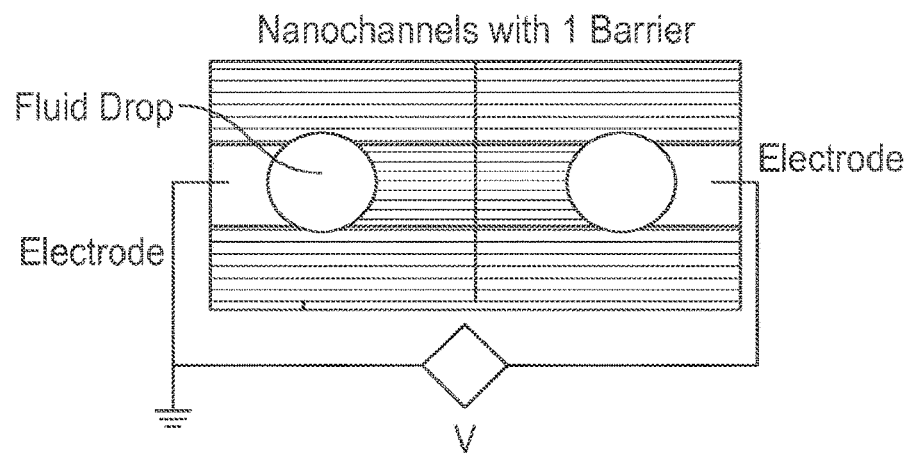
FIG. 7 is a schematic illustration of a structure as described herein including a porous barrier interrupting the nanochannels.
Figure 8:
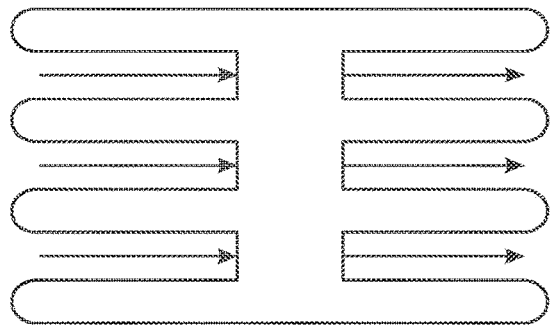
FIG. 8 is a top-wise schematic illustration of sample flow through the nanochannels of FIG. 7.
Figure 9:
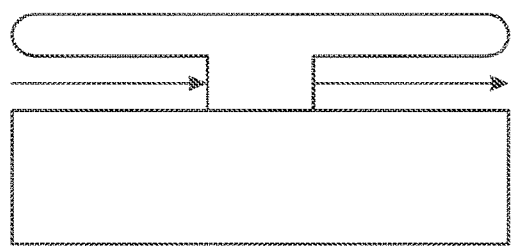
FIG. 9 is a side view of sample flow through a nanochannel of FIG. 7.

Furthermore, a simple optical exposure before the spin coating step enables the introduction of porous regions (barriers) along the nanochannels. As shown in FIG. 7-9, these barriers can be used to accumulate molecules of interest in the sample and localize the translocation of those molecules through the roof.

It will be appreciated that some applications that utilize the above-described nanochannels would benefit from the ability to specifically control the density of the nanopores in the nanochannel roof. For example, it might be desirable to reduce the density of the nanopores, so as to reduce or eliminate unwanted leakage or transport of samples through the roof and/or enabling the translocation, transportation, or identification of specific long chain molecules of interest including, for example, single stranded DNA (ssDNA), RNA and proteins. Accordingly, the present disclosure provides for the formation of tortuous nanopores that are formed in the nanochannel roof and which can be further decreased in size and density bystandard film deposition processes such as e-beam evaporation, sputtering, CVD and/or conformal atomic layer deposition (ALD). (The film deposition both closes some of the pores, reducing the density, and also decreases the sizes of the remaining pores allowing only a single long chain molecule to transit at a time.)

According to various embodiments, after the tortuous nanopores are self-assembled in the roof, the roof is partially sealed, by which it is meant that some, but not all, of the externally accessible pores formed by the self-assembly and calcination of the nanoparticles are sealed. According to various embodiments, the pores may be sealed using either CVD, ALD, or a combination of both. For example, as described in greater detail below, a combination of CVD and ALD can be used to close the smallest pores to prevent leakage or penetration of the sample through the roof, control pore density, and ensure compatibility with optical resolution.

Figure 10:
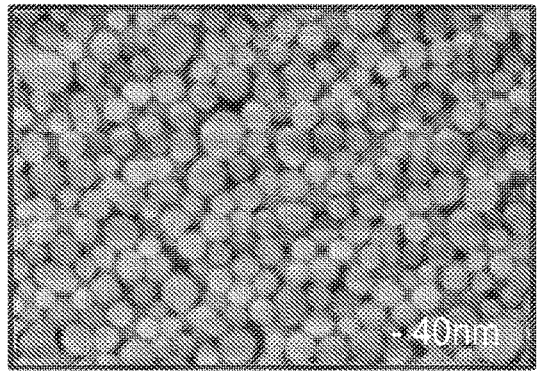
FIG. 10 is a high resolution SEM image of a nanochannel roof fabricated using the methods provided herein.
Figure 11:
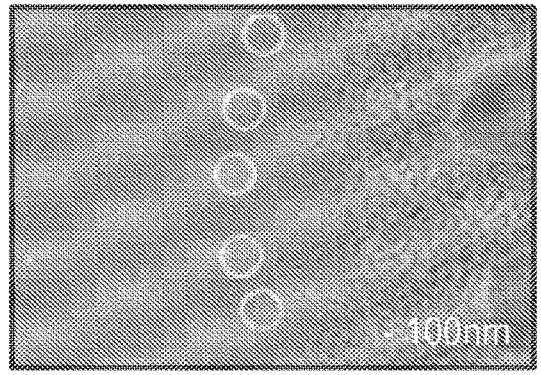
FIG. 11 is a high resolution SEM image of the roof of FIG. 10 roof after deposition of $Si_3N_4$ CVD layer (partially etched on the right side to form the reservoir). The white circles mark pores that are just appearing as the etch progresses.
Figure 12:
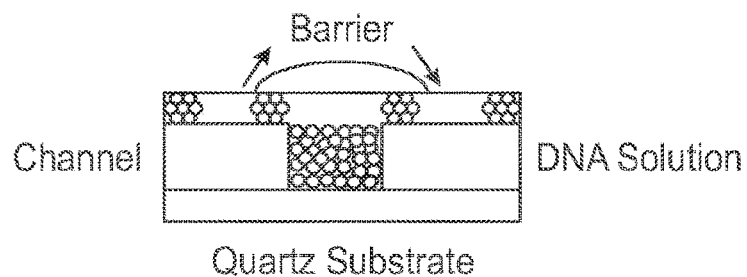
FIG. 12 is a schematic illustration of a nanochannel structure as described herein demonstrating liquid penetration through the roof over a barrier formed in the nanochannel.
Figure 13:
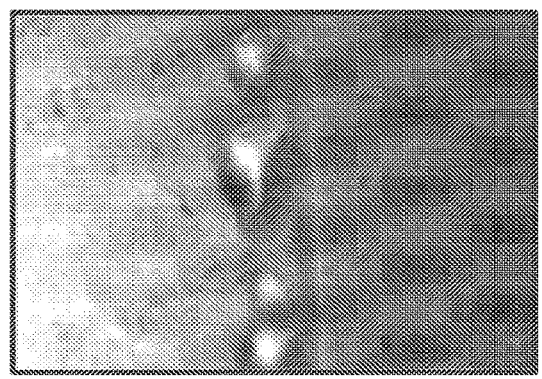
FIG. 13 is an image of a sample with nanochannels and one 3 µm barrier.
Figure 14:
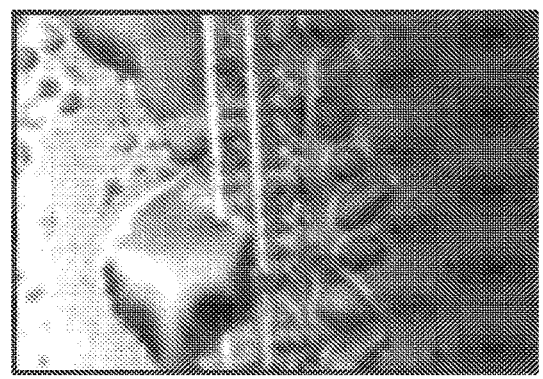
FIG. 14 is an image showing drops of fluid along three 3-µm wide barriers with an electric field applied.

FIG. 10 is a high resolution SEM image of the porous roof; while FIG. 11 is a high resolution SEM image of the porous roof after deposition of a plasma-enhanced CVD silicon nitride film. In FIG. 11, the structure is partially etched on the right side to form a reservoir and to provide access to the sides of the nanochannels. The white circles mark pores that are just appearing as the etch progresses. The deposition tool used for the CVD puts down a porous layer, much like a blanket of snow, over the NPs. This process can be tuned for varying degrees of film porosity by variation of the deposition conditions. An example of the process parameters used for the CVD deposition of silicon nitride include: T=300° C.; pressure of 600 mTorr; RF power of 50 W; and flow rates of $[SiH_4]$ 30 ccm, $[NH_3]$ 50 ccm, $[N_2]$ 15 ccm. For the as-deposited roof, both the dispersion of the nanoparticle size and the dispersion of nanopore sizes is evident. It is important to keep in mind that this is a tortuous nanopore, and the opening dimension is not necessarily the tightest constriction along the pore. As can be seen in FIG. 11, the CVD film has largely covered the larger scale (~10's of nm linear dimension) nanochannel pores, but some of the larger ones are beginning to be evident in the transition region between the as-deposited and the etched regions as marked by the white circles. The density and dimensions of these pores can be controlled by: 1) adjusting the NP size dispersion, 2) the use of ALD before the CVD step to seal the majority of the pores in the NP roof, 3) the use of different overlayers (either dielectric or metal prior to the active metal layer). Even in this first example, for which no optimization has been attempted, the nanopore density is close to the required separation of ~λ to allow far-field resolution of the exit of each tortuous nanopore. The evaporation of buffer solution from the roof is evidence that the roof is porous, and this evaporation time has been controlled over several orders of magnitude with the deposition and ALD steps outlined below. When a bias is applied across the nanochannels, particularly with a barrier, there are isolated drops of fluid (and DNA) that emerge from the pores and decorate the top of the roof (FIGS. 12-14). Note that the drops are not contiguous, suggesting that the largest pores are well separated.

Figure 15:
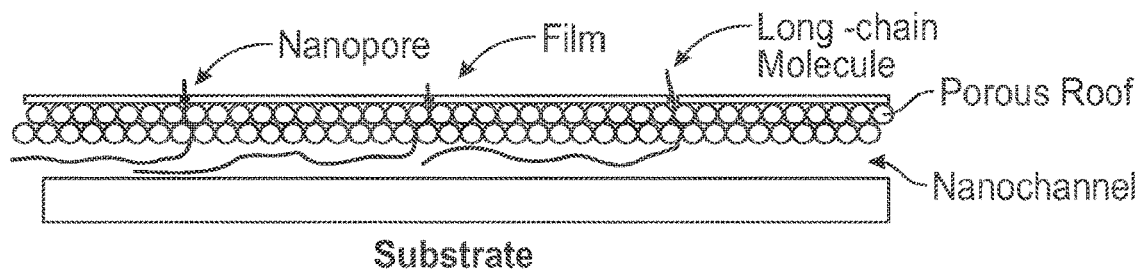
FIG. 15 is a schematic illustration of a nanopore structure of the present disclosure with at least one manufactured nanopore assembled on the roof of the tortuous nanopore structure.

According to various embodiments, a nanopore structure with at least one manufactured nanopore can be assembled on the roof of the tortuous nanopore structure. This could be a dense nanopore structure such as a graphene sheet or a sparse nanopore structure such as a nitride film in which nanopores are fabricated, e.g. by ion-milling, either before or after application of the film to the tortuous nanopore structure. Since the goal is the read of long-DNA (as well as RNA and proteins) molecules, up to ~50,000 bases or ~10 μm of natural length, the tortuous nanopores structure reduces the DNA translocation speed through the conventional registering nanopore. (FIG. 15).

Figure 16:
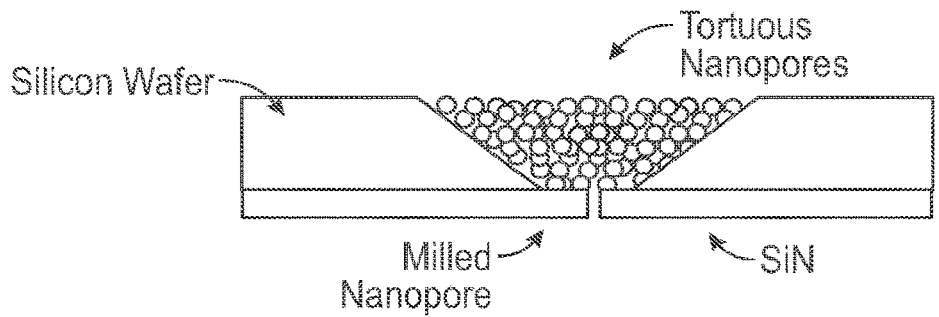
FIG. 16 is a schematic illustration of an embodiment wherein a tortuous nanopore structure is applied to an existing nanopore structure.

An alternative embodiment is to apply the tortuous nanopore to an existing nanopore structure, for example an ion- or electron-milled pore in a nitride film (FIG. 16). This could be done by applying a nanoparticle suspension to one side of the pore and allowing it to dry to form the tortuous pathway for the DNA or similar long-chain molecule. The existing nanopore diameter can be adjusted so that ALD can be used both to restrict the translocation through the tortuous pathway through the nanoparticles and to decrease the diameter of the nanopore in the film. The pore in the film can be fabricated either before or after the formation of the tortuous pathway.

The evaporation rate from the pores provides a convenient measure of the pore density. For the as-fabricated nanochannels (prior to the CVD and ALD treatments), when a drop of a buffer solution is introduced to the reservoirs, the fluid penetrates only a small distance, <1 mm, into the nanochannels before the fluid has evaporated (in low laboratory humidity). After the treatments discussed below, the penetration distance into the pores is increased to ~1 cm.

In addition to adjusting the nanopore density and pore size, the addition of a non-porous secondary optically transparent roof in close proximity to the porous roof provides a means to adjust the local humidity and hence control the evaporation rate out of the nanochannels. This roof can provide multiple enhancements to the device: 1) it can provide a micro- or macro-flow channel for the buffer/molecular solution on exiting the nanopores to allow removing them from the region of the pore and controlling the local humidity at the nanopore; 2) it can provide an optical quality surface for far-field optical measurements; and 3) with the addition of a transparent electrode such as ITO, or a gridded electrode structure, it can allow for further manipulation of the quasi-static electric fields in the vicinity of the tortuous nanopore to control the translocation velocity. (See e.g., FIG. 33.)

Various approaches can be used to reduce the density of these pores and therefore the evaporation rate from the channels. An exemplary approach utilizes a combination of $SiO_2$ CVD and atomic layer deposition (ALD) Evaporation can be estimated by the distance of liquid penetration through the channels. If we put a drop of liquid on the porous roof we can see that penetration of liquid through the channels is approximately 1.5- to 2.5-mm and DNA solution easily penetrates through roofs with ~15 nm pores at the same distance. We observed the same penetration distance of solution and DNA if we put the drop into the well. Chemical vapor deposition (CVD) of an 80- to 120-nm film of $Si_3N_4$ or $SiO_2$ over the roof reduces the evaporation and provides penetration of solution with DNA up to 3- to 4-mm. A further application of 10- to 20-nm thick atomic layer deposition (ALD) of silica ($SiO_2$) or alumina ($Al_2O_3$) over the CVD deposition reduces the roof pore size further and provides liquid penetration up to 5-8 mm.

Figure 17A:
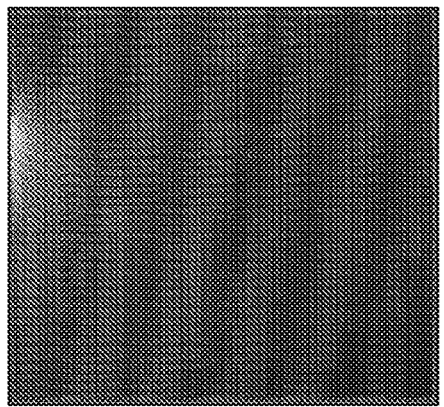
FIG. 17A is an image showing the fluorescence from a drop of buffer/λDNA placed on top of the roof of an $HfO_2$ ALD nanochannel approximately 15 seconds after the drop was placed on the roof.
Figure 17B:
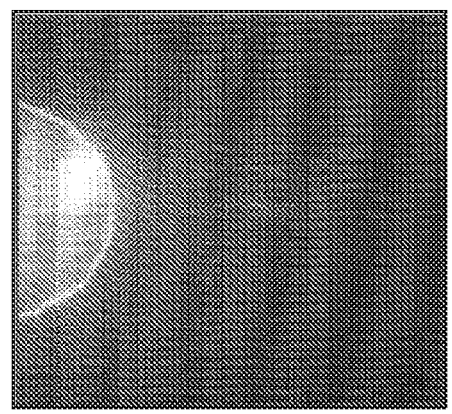
FIG. 17B is an image of the drop of FIG. 17A 5 minutes after the drop was placed on the roof.
Figure 17C:
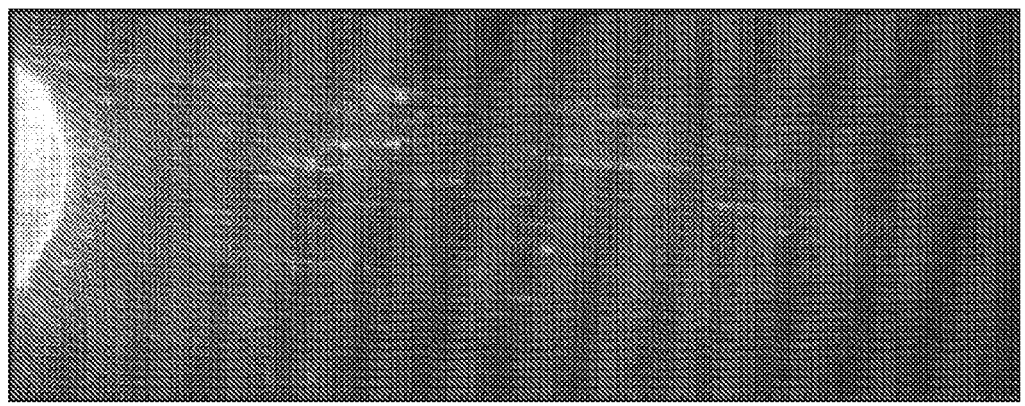
FIG. 17C is an image of the drop of FIG. 17A 10 minutes after the drop was placed on the roof.

Other successful approaches utilize $HfO_2$ and $Al_2O_3$, which can be, for example, deposited using standard semiconductor protocols for ALD. FIGS. 15A-15C show the fluorescence from a drop of buffer/λDNA placed on top of the roof of an $HfO_2$ ALD nanochannel as it penetrates the roof. FIG. 17A shows the drop approximately 15 seconds after it is placed on the roof. FIG. 17B shows the drop after 5 minutes and FIG. 17C shows the drop after 10 minutes. The λDNA penetrates through the remaining pores in the roof and then spreads by diffusion along the nanochannels. Note the long time scale of up to 10 min. for the evolution of this distribution. This suggests that: 1) the density of pores can be substantially reduced with sufficient size for long dsDNA penetration, 2) there is evidence that individual λDNA molecules are translocated, and 3) that the translocation time (without any applied bias) is sufficiently long for sequencing as a result of the tortuous pathway.

Of course it will be appreciated that many, if not most, applications of the presently described device will implement a detection mechanism for detecting the molecule of interest and that many suitable mechanisms are well known and can be used with the presently-described device. However, it will also be understood that in particular, DNA sequencing applications require very exacting detection methods that are capable of achieving single base resolution, and thus the present disclosure provides novel structures and enhance and enable detection at levels suitable for DNA sequencing applications.

As is well known, a difficulty in achieving both single base sensitivity and resolution with far field optical techniques is associated with the large size of the photon, which can be focused to scales of ~½ the optical wavelength ~300 nm, approximately two orders of magnitude larger than the ~0.3 nm linear dimension of the each of the DNA bases. This can be addressed with a field enhancement structure that increases the local field intensity in a small volume. Typically these field enhancement structures are metals where excitation of surface plasma polaritons leads to a strong field enhancement in a small local region. This is the basis of surface enhanced Raman scattering, which has been well studied for many years.

As a first embodiment for localizing and enhancing the photon fields, a metal film can be deposited on the top of the nanochannel roof. If the film is deposited with a directional process such as, but not limited to, electron beam evaporation, the film will be conformal with the fine structure of the roof, and in particular will have holes that are aligned with and on the scale of the tortuous nanopore exits. This is a self-aligned process, guided by the directional deposition and the topology of the nanochannel roof, so no lithography step is required.

Alternative localized metal structures are: a dipole structure (two metal triangles pointed at each other with a small gap between them) or a "C" aperture (a metal loop with a small gap). Each of these produces large fields at the gap under optical excitation. These structures are defined by a lithographic step, so they are appropriate for situations in which the location of the nanopore is known a priori such as in the case of manufactured nanopores produced by processes such as electron-beam lithography or ion-beam milling.

As stated above, according to another embodiment, base-level optical resolution can be provided by an engineered multi-level metal-insulator-metal (MIM) plasmonic structure that is self-assembled to the nanopores, providing a simple, inexpensive, and self-aligned fabrication process. The <1 nm insulator thickness provides the necessary base-level resolution and the wide pore spacings allow for independent far-field optical readout, providing a massively parallel sequencing capability. Furthermore, both labeled (fluorescence) and unlabeled (SECARS) optical readout mechanisms can be used with this system. This is related to the small gaps between aggregated colloidal Au and Ag nanoparticles which gives rise to single molecule Raman scattering detection. Here, the gaps are engineered by to be aligned to the exits of the tortuous nanopores on the roof of the nanochannels.

The MIM can be deposited by a combination of anisotropic and isotropic deposition processes and can be self-aligned to the nanopores. For example, a thin metal film can first be deposited by e-beam evaporation or sputtering, a directional process that will not close the nanopore. Then a thin (e.g., ~1 nm) insulator film can be deposited by atomic layer deposition, a conformal deposition process that will further reduce the nanopore diameter. Finally, a second metal film can be deposited by a directional process. This provides a self-aligned, massively parallel nanofabrication technology that bypasses the need for any high-resolution, ~1-nm lithography and allows far-field optical recording of near-field processes with the necessary resolution. The MIM structure both provides strongly enhanced electromagnetic fields, allowing single molecule detection, and the near-field nanoscale resolution necessary to resolve individual bases in, for example, single-strand DNA (ssDNA). According to various embodiments, the motion of the sample through the nanochannels and nanopores is slowed by the tortuosity of the nanopores and can be further controlled by voltages applied to the channels, the MIM, and to control electrodes, which could be placed, for example, above the nanochannel roof.

Figure 18:
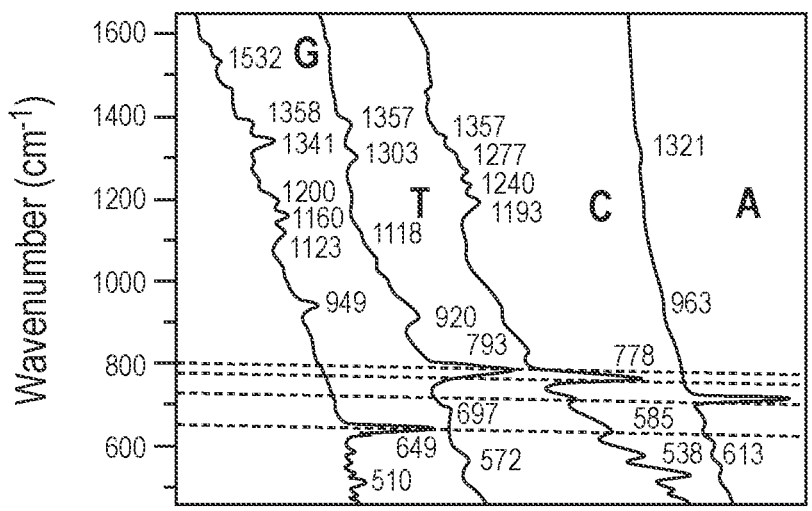
FIG. 18 is a graph showing Spectra offset for visibility. The four dotted lines mark unique spectral identifiers. (Graph is modified from a version shown in Ref 57)

The above-described technique can thus be used to form Raman "hot-spots" in those embodiments where a Raman spectroscopy-based detection method is used. Surface Enhanced Raman Scattering (SERS) and surface-enhanced coherent anti-Stokes Raman scattering (SECARS) are related techniques that offer the potential for both enhanced signal levels that have already demonstrated single molecule level sensitivities. Both techniques rely on localized "hot-spots," often at the interstices between metallic particles (for example in colloidal aggregates). These hot-spots serve two essential purposes: 1) to ensure large electromagnetic fields (SERS, a two-photon process, scales as $\sim E^4$ and SECARS, a four-wave mixing process, as $\sim E^8$) providing the single molecule sensitivity and 2) to localize the interaction volume to single-base level dimensions—many orders-of-magnitude smaller than $\lambda^3$—providing the necessary single base resolution. This separation can be engineered by the MIM structure described above. Thus, field enhancements of 30, which are quite reasonable for nanostructure metals, lead to Raman enhancements of $\sim 10^6$ and to SECARS enhancements of $10^{12}$. Simply stated, Raman scattering is a mixing between an incident photon at frequency ci and a molecular vibration at frequency ν, to provide an anti-Stokes signal at $\omega_{1+}\nu$ and a Stokes signal at $\omega_1-\nu$. The intensity, of the anti-Stokes signal is proportional to the occupation number of the molecular vibration, and is generally small at room temperature where $\kappa T \leq \nu$, where $\kappa$ is Boltzman's constant and T the absolute temperature (Kelvin). Coherently driving the excitation using two coherent sources at frequencies $\omega_1$ and $\omega_1-\nu$ and detecting the signal at $\omega_1+\nu$ provides another enhancement of the Raman signal. This is known as coherent anti-Stokes Raman scattering or CARS. By using a broadband second (lower) laser frequency (for example a supercontinuum), we can probe all four bases simultaneously. CARS is a four-wave mixing process (described by a third order nonlinear susceptibility, $\chi^{(3)}$). An alternate approach is to provide a source of phonons that directly excite the vibrational mode. These techniques maybe preferred in some cases as they are label-free and do not require any manipulation of the unknown DNA before sequencing. Raman spectra of each of the four DNA bases are well known, and offer readily separable signatures as shown in FIG. 18 (modified from a figure in reference 57). Fluorescence labeling techniques have been demonstrated[58] and may be used as an alternate sequencing approach. Fluorescence, as spontaneous Raman scattering (SERS), involves two photons, and is enhanced ($E^4$) and localized by plasmonic effects.[59]

Figure 19:
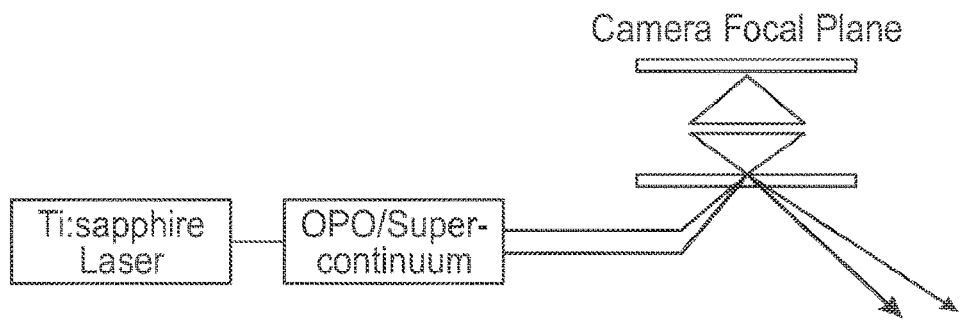
FIG. 19 is a schematic illustration of a detection scheme according to the present disclosure wherein the pump and Stokes excitation beams are generated with a Ti:sapphire laser and a nonlinear process.

A schematic optical scheme is shown in FIG. 19. According to an embodiment, the pump and Stokes excitation beams can be generated with a Ti:sapphire laser and a nonlinear process such as an optical parametric oscillator or a supercontinuum generation scheme. The advantage of the supercontinuum is that all four bases can be probed simultaneously (using, for example, dielectric filters to separate the anti-Stokes wavelengths). According to an exemplary arrangement, the laser illuminates through the nanochannel substrate, so that most of the pump light is reflected by the MIM structure, simplifying the isolation of the SECARS signals. Since the device is probing a set of single bases, each localized to a resolution much smaller than the optical wavelength, there is no phase-matching requirement as in traditional CARS, and the radiation is emitted in a dipole radiation pattern. A judicious choice of the illumination geometry suppresses the non-resonant four-wave mixing signal from the substrate and nanochannel materials, enhancing the desired SECARS detectivity. According to an embodiment, the SECARS signal can be collected with a high-NA objective and imaging onto either a single detector for photon counting or onto a high-sensitivity camera(s) for massively parallel multi-pore analysis. Since, by design, the pores are separated by more than the resolution limit of the objective, the measurements for each channel are optically independent.

According to various embodiments, it is generally desirable for the Raman hot-spot to be sufficiently small and aligned with the exit of the tortuous nanopore so that the bases transit sequentially through the hot-spot. The presently described technique takes advantage of a self-aligned fabrication technique to ensure this overlap. Deposition processes such as e-beam evaporation and sputtering are directional, so that when applied to the rough surface of our ALD coated nanoparticle roof, holes will form in a deposited metal film just at the pore locations, serving to define the locations of the hot spots. Additional localization can be enforced by fabricating a MIM structure. This can be done using ALD to sequentially deposit a very thin dielectric layer (e.g., ~0.5 to 1 nm) on the metal followed by a second metal layer, either with ALD or with directional deposition. The highly nonlinear SECARS process further reduces the extent of the hot-spot, providing the required single base resolution. As a result of the stochastic distribution of pore sizes, there might be some pores that allow translocation of more than one molecule, for example more than one ssDNA strand simultaneously, or of residual dsDNA strands. Fortunately, these can be detected with temporal coincidences of reads of two bases in the same location, and these pores can be ignored computationally, without requiring any hardware modifications.

According to various embodiments, SECARS enables nanoscale-level discrimination, even between bases in ssDNA. While the interaction leading to the Raman signature is confined in the near-field by the small dimensions of the apertures in the MIM and the spacing between the two metal films, the readout is in the far-field providing a massively parallel readout where each camera pixel can independently and simultaneously address individual nanopores. In a fully engineered system, long reads (>50 kilo-bases) with up to one million nanopores, separated by more than the resolution element of the observation microscopy, and a camera operating at 30 frames/s giving a throughput of as much as $10^{11}$ bases per hour is possible. Furthermore, the fluidic chip can be inexpensively produced and is designed to be field replaceable.

As stated above, according to some embodiments, the presently disclosed apparatus can be used for the rapid and inexpensive separation, transportation, detection, and/or sequencing (referred to herein collectively as "manipulation") of nucleic acids, including, for example, genomic DNA. According to this embodiment, each nanopore in the roof structure becomes an independent DNA translocation site that can be optically resolved in parallel (~1M per mm$^2$). Moreover, it will be understood that a variety of potentials could be applied across the device to control the DNA translocation. For example, as described in greater detail below, three or more potentials could be applied: along the nanochannels; between the nanochannels and the plasmonic readout structure; and above the plasmonic readout structure to provide exquisite control of the DNA translocation.

Figure 20A:
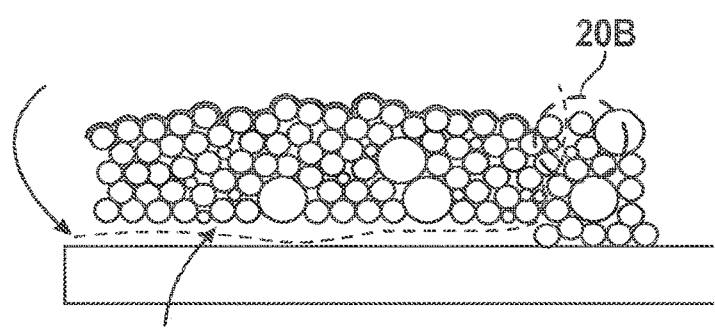
FIG. 20A depicts an exemplary method of DNA manipulation according to an embodiment of the disclosure.
Figure 20B:
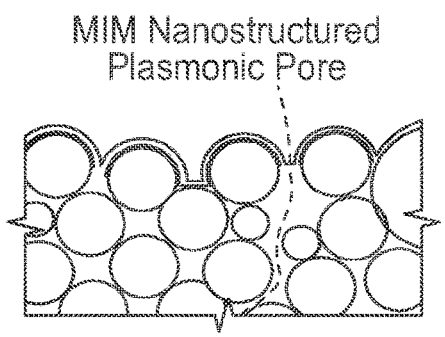
FIG. 20B is a close up of the structure shown in FIG. 20A to better show the location and presence of the Metal Insulator Metal (MIM) structure.

FIGS. 20A-20B depict of an exemplary method of DNA manipulation according to an embodiment of the disclosure. The DNA enters the nanochannel from the reservoir (not shown) on the left and is uncoiled by the dynamics in the nanochannel. Three sizes of silica nanoparticles (grey-scale differentiated) are shown to represent the dispersion in NP size. The NPs form a close-packed quasi-hexagonal lattice disturbed by steric effects as a result of the size dispersion, giving rise to a non-uniform set of tortuous pathways through the roof. An ALD process, represented by the dark borders on the NPs, closes the bulk of the nanopores (as evidenced by the dramatic reduction in evaporation rate through the roof following the ALD treatment), resulting in a density of remaining nanopores that is compatible with far-field optical resolution. The ALD can be controlled so that the majority of the remaining tortuous nanopores are sufficiently small that only a single ssDNA strand can pass through at a time. Finally, a metal-insulator-metal (MIM) structure (in expanded view in FIG. 20B) localizes the enhanced electromagnetic fields and provides single base measurement capability.

Figure 21:
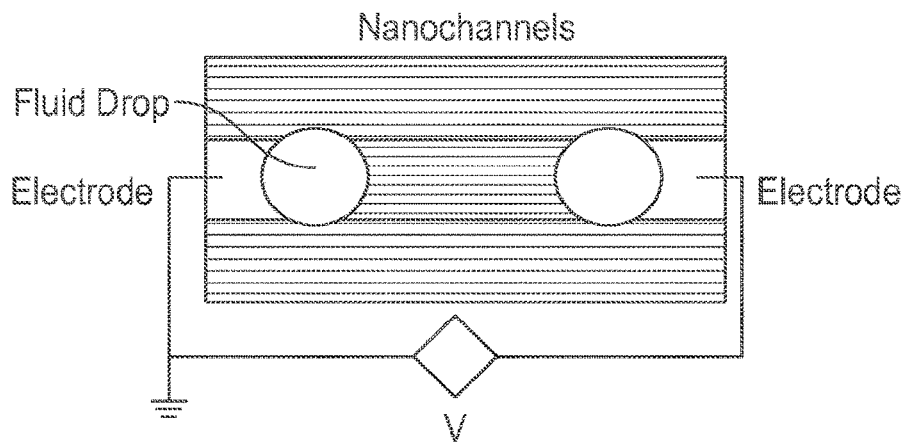
FIG. 21 is a schematic illustration of a typical experiment where a DNA-containing solution is directly applied to the entrance of a nanochannel array.
Figure 22:
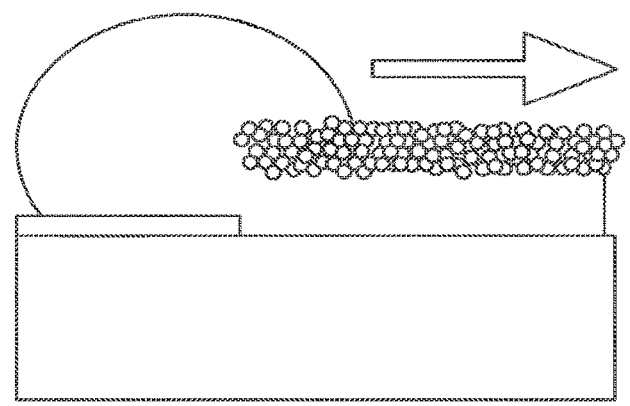
FIG. 22 is a schematic illustration showing DNA penetration in the nanochannel of FIG. 21.
Figure 23:
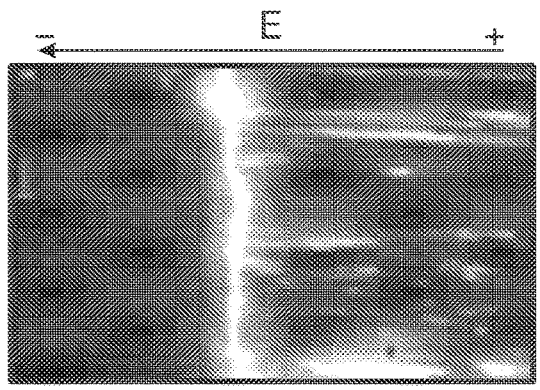
FIG. 23 is an image of DNA entering the nanochannel when voltage is applied.
Figure 24:
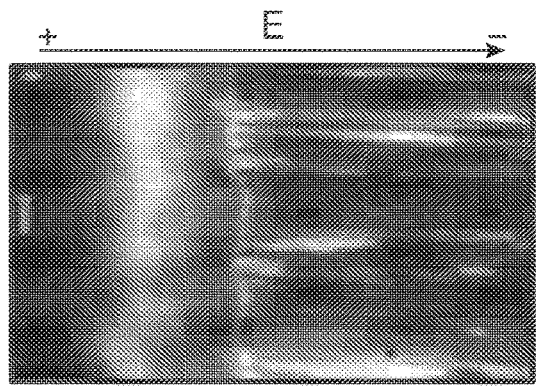
FIG. 24 is an image of DNA moving out of the nanochannel when the voltage is reversed.

A typical experiment is illustrated in FIGS. 21-22, where a DNA-containing solution is directly applied to the entrance of a nanochannel array. A dyed (YoYo1) $\lambda$DNA solution is applied to one side of the channel and a buffer solution (without DNA) to the other end. FIG. 22 DNA penetration in the nanochannel. The image of FIG. 23 shows DNA entering the nanochannel when voltage is applied while FIG. 24 shows DNA moving out of the channel when the voltage is reversed.

Figure 25:
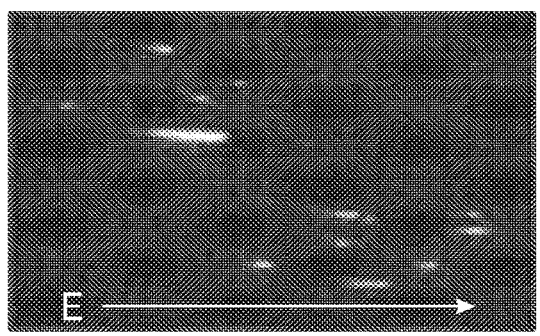
FIG. 25 is an image showing that an electric field applied in the direction of DNA movement stretched the molecules towards the positive electrode over many 10's of µms.
Figure 26:
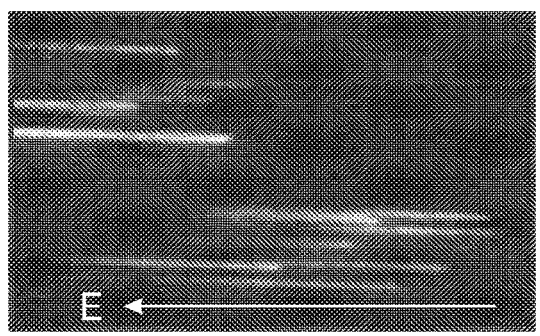
FIG. 26 is an image showing that an electric field applied in the opposite direction (from FIG. 25) compressed the DNA to 2 µm.
Figure 27:
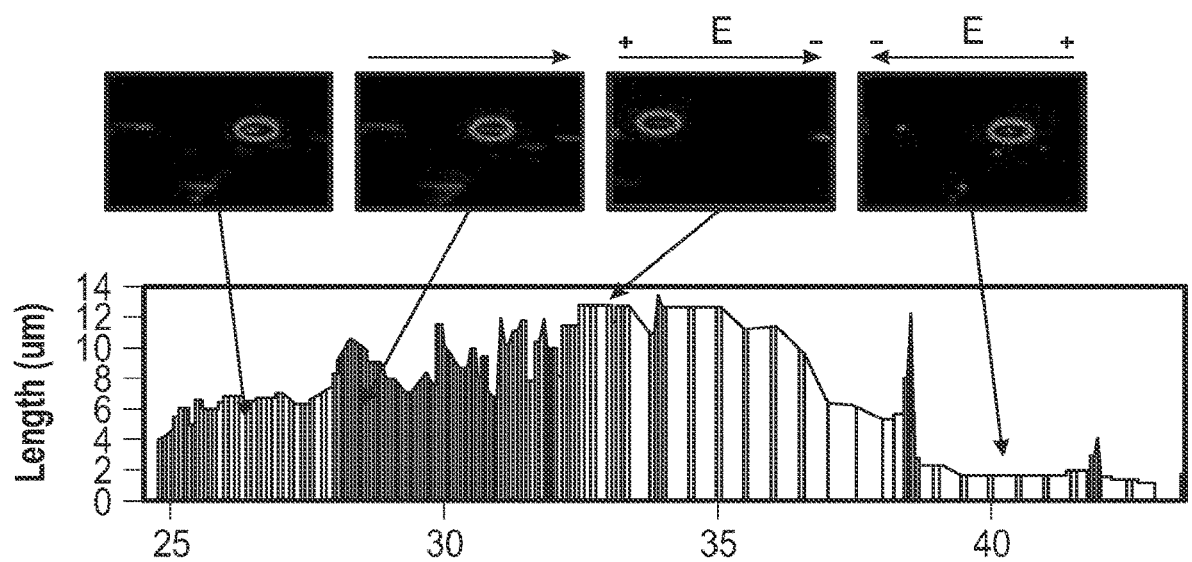
FIG. 27 shows data demonstrating the movement and stretching of DNA that can be achieved using the herein described nanochannels by applying different potentials across the device.

In order to further investigate the influence of an electric field on dsDNA behavior in the herein described nanochannel, we have monitored the stretching of ds-DNA. The results demonstrate that an applied electric field causes the negatively charged dsDNA to migrate towards the positive contact. Some DNA molecules appear stuck in blocked channels and accumulate. An applied electric field in the direction of DNA movement stretched the molecules towards the positive electrode over many 10's of μms (FIG. 25). Whereas, an electric field in the opposite direction compressed the DNA to 2 μm (FIG. 26). The data shown in FIG. 27 demonstrates the movement and stretching of DNA that can be achieved using the herein described nanochannels by applying different potentials across the device. This enables the user to control the base spacing by selecting the appropriate direction and applied voltage of the potential.

Those of skill in the art will be familiar with various methods for preparing DNA libraries for sequencing. Exemplary methods and commercially available kits that may be used alone or in combination include the Qiagen DNA isolation kit for purifying dsDNA and the Promega Ready Amp kit for ssDNA isolations. Long ssDNA isolation can be performed using alkali treatment, neutralization of the pH, and maintenance of the single stranded stare with an optimized formamide buffer. Commercial kits are also available from Promega. Alternatively, asymmetric PCR can be used to generate ssDNA. There are a number of publications that describe the generation of ssDNA by asymmetric LATE-PCR, and this is a robust simple way to generate ssDNA. Alternatively, it may be desirable to first generate a sequencing library that is 10-20 kb and amplify the library with an asymmetric primer ratio. The ssDNA can then be isolated prior to application to the chip. The nanochannel chip can be run with 50% formamide and at an elevated temperature to encourage ssDNA entry into the channels. Due to entropic forces, the ssDNA should elongate along the channel without secondary structure.

As an alternative to asymmetric PCR, it is also possible to use 50% biotinylated primers to capture amplified library fragments. To isolate ssDNA, fragments can be captured with streptavidin coated beads. The Library molecules that contain a single biotinylated primer and a single non-biotinylated primer can be eluted from the beads with a 0.1M NaOH wash. The pH of the supernatant is then neutralized, and the ssDNA fragments loaded into the nanochannels with a 50% formamide buffer. Yet another approach involves exonuclease digestion in the nanochannels. Using this approach, it is possible to load very long (up to 50 kb) fragments with minimal library preparation.

Figure 28:
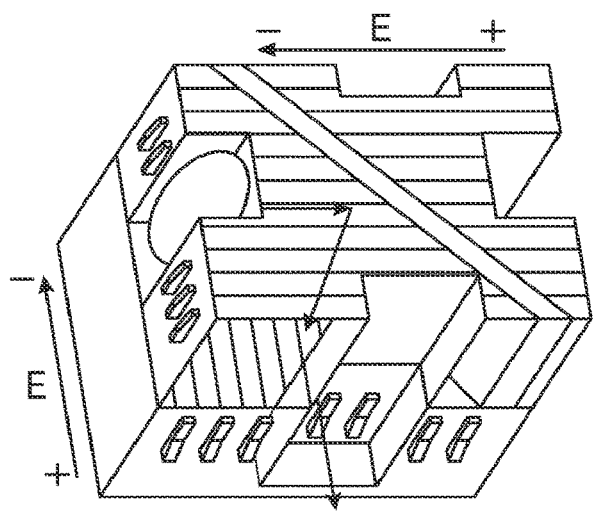
FIG. 28 is a schematic illustration of two-tiered nanochannels engineered with the different tiers positioned in orthogonal directions.
Figure 29:
FIG. 29 is an image showing λDNA diffusion between levels of a two-tiered nanochannel structure.

As stated above, the presently described methods enable the production of multileveled (i.e. tiered) nanochannels. FIGS. 28 and 29 depict two-tiered nanochannels engineered with the different tiers positioned in orthogonal directions. The use of two-tiered nanochannels allows for the controllable introduction of an exonuclease, such as the T7 exonuclease (5'→3' exonuclease), in the vicinity of the nanopores in order to digest a single strand of ds DNA. After the exonuclease has digested one of the strands, the ssDNA will be relatively resistant to exonuclease activity. This leaves the ssDNA in the nanochannel with the 3' end leading into the nanopore. The 3' end can then advance through a tortuous nanopore, enabling the sequence to be resolved using the methods described below.

According to various embodiments, the nanochannels described herein enable dsDNA and/or ssDNA to move randomly through the tortuous nanopores in the roof of the nanochannels. In some embodiments it may be desirable to optimize this translocation to ensure a desired spatial density (for example, ~1 $\mu m^{-1}$) along the nanochannel to allow far-field optical interrogation of individual nanopores.

Figure 30:
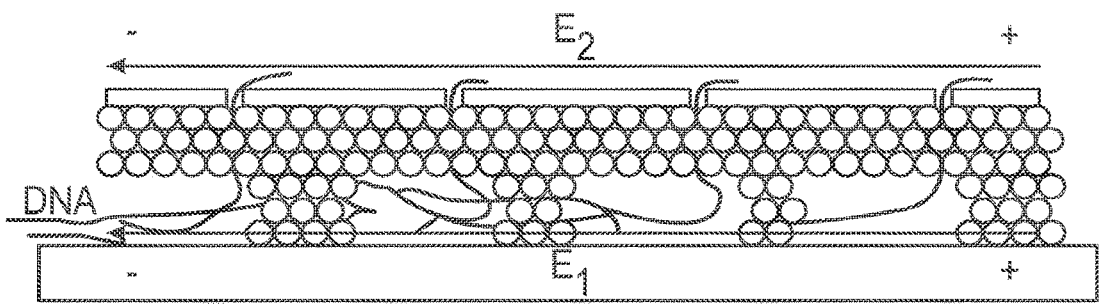
FIG. 30 is a side view of a nanochannel according to an embodiment of the present disclosure.
Figure 31:
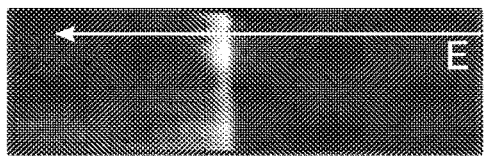
FIG. 31 is an image showing DNA accumulation at a barrier within a nanochannel.
Figure 32:
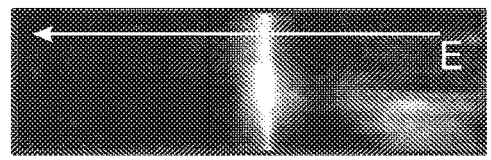
FIG. 32 is an image showing movement of DNA through a barrier.

Our preliminary data has shown that DNA moves out of the nanochannels through the pores in the roof. The escape of DNA from the nanochannels preferentially occurs when the channel is interrupted by a barrier as demonstrated in FIGS. 30-32, where FIG. 31 is an image showing DNA accumulation at a barrier within a nanochannel and FIG. 32 is an image showing movement of DNA through a barrier. Accordingly, in some embodiments it may be desirable to construct barriers in the channels. In some embodiments it may be desirable for these barriers to have different thicknesses. For example, one design can have thin barriers at the beginning of the nanochannel and thicker barriers toward the end (see, e.g., FIG. 30).

Figure 33:
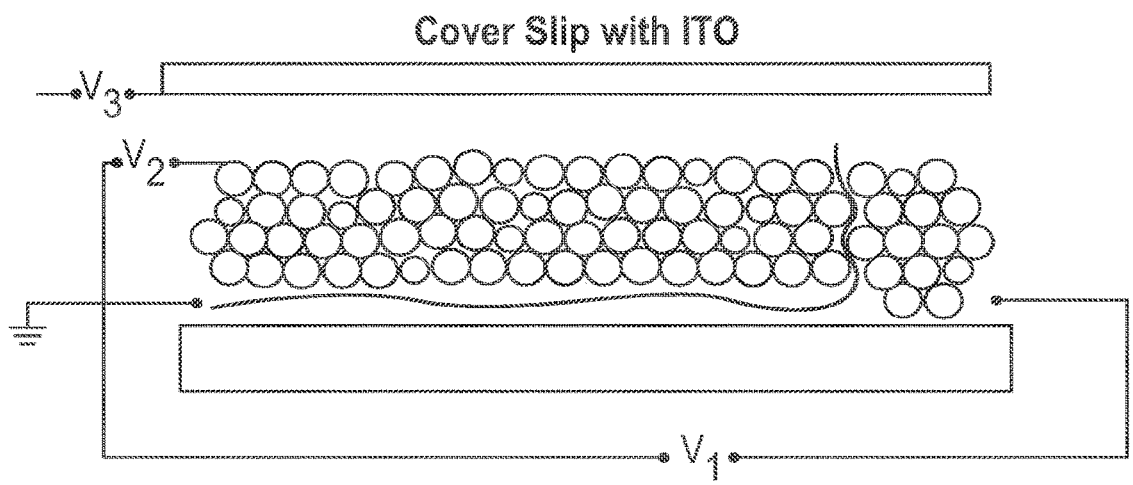
FIG. 33 is a schematic illustration of an electrical design that could be used with the structures described herein.

According to various embodiments, multiple voltages can be applied to impact the translocation. As shown in FIGS. 21-32, voltages are routinely applied along the nanochannels to control the position and conformation of the λDNA. In addition, and as shown in FIG. 33, it may be desirable to add a bias to the nanoplasmonic structure, and an independent voltage to a transparent conducting layer [indium-tin-oxide (ITO)] located in the fluid volume above the plasmonic structure. All of these can be AC voltages with a DC bias. In electrical terms, this is a four-terminal device, giving us control over the translocation through the tortuous nanopores.

Figure 34:
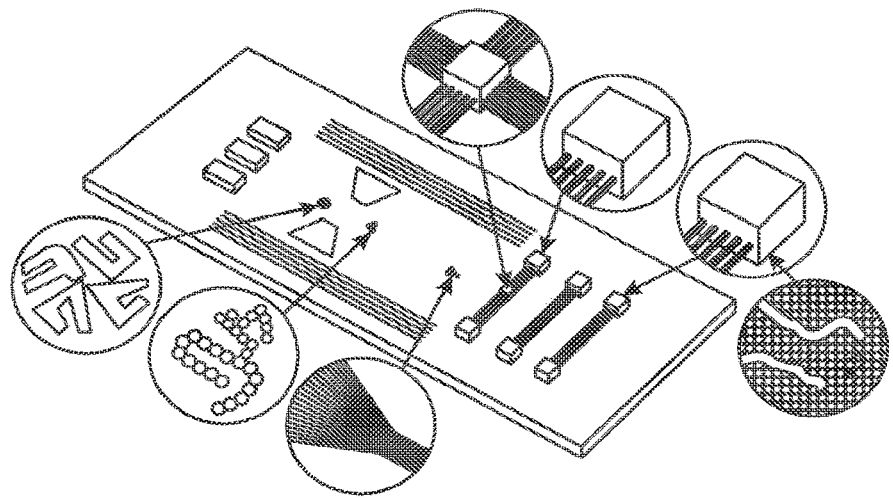
FIG. 34 is an image of a possible lab-on-a-chip design incorporating the nanochannels and other structures described herein.

Turning to FIG. 34, the present disclosure also contemplates a fully integrated lab-on-a-chip design in which a single device or "chip" fluidly connects the presently described structures via flow homogenization channels which are able to connect the nanochannels described herein with structures, including, if needed, microchannel sized structures, intended to prepare the sample.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise.

What is claimed is:

1. A method for manipulating long chain target molecules using a nanochannel covered with a porous roof comprising tortuous sealed and unsealed nanopores, the method comprising:
   introducing a buffer solution into the nanochannel;
   applying a first voltage potential across the nanochannel to move the long chain target molecules in the buffer solution through the nanochannel in a first direction;
   translocating the long chain target molecules through the unsealed nanopores in the porous roof of the nanochannel, wherein the porous roof further comprises a field enhancement structure aligned with the unsealed nanopores; and detecting and sequencing individual moieties of the long chain target molecules that translocate through the unsealed nanopores using Raman scattering.

2. The method of claim 1, further comprising:

applying a second voltage potential along the nanochannel by reversing the first voltage potential, such that the long chain target molecules move through the nanochannel in a second direction opposite to the first direction; and detecting the long chain target molecules after applying the second voltage potential.

3. The method of claim 1, wherein applying a first voltage potential comprises applying an alternating current (AC) voltage potential having a direct current (DC) bias.

4. The method of claim 1, wherein translocating the long chain target molecules comprises applying a second voltage potential along the unsealed nanopores to control a translocation velocity of the long chain target molecules through the unsealed nanopores.

5. The method of claim 1, wherein applying a first voltage potential comprises moving the long chain target molecules through the nanochannel to a barrier disposed in the nanochannel, prior to translocating the long chain target molecules through the unsealed nanopores.

6. The method of claim 1, wherein applying a first voltage potential further comprises routinely applying multiple voltage potentials along the nanochannel.

7. The method of claim 1, wherein applying a first voltage potential further comprises moving the long chain target molecules across the porous roof in the first direction.

8. The method of claim 1, wherein:

the long chain target molecules comprise single-stranded or double stranded nucleic acids; and detecting the long chain target molecules comprises detecting a base sequence of the long chain target molecules.

9. The method of claim 1, wherein introducing a buffer solution comprises applying the buffer solution to the porous roof, such that the buffer solution passes through the unsealed nanopores and enters the nanochannel.

10. The method of claim 1, wherein:

the long chain target molecules comprise single-stranded (SS) nucleic acids;

introducing a buffer solution comprises introducing a buffer solution comprising double-stranded (DS) nucleic acid molecules into the nanochannel; and the method further comprises introducing an exonuclease into the nanochannel to digest the DS nucleic acid molecules and form the long chain target molecules.

11. The method of claim 1, wherein:

the long chain target molecules comprise single-stranded (SS) nucleic acids; and introducing a buffer solution comprises introducing a buffer solution comprising the SS nucleic acids.

12. The method of claim 1, wherein:

the long chain target molecules comprise single-stranded (SS) nucleic acids; and the buffer solution comprises a formamide buffer.

13. The method of claim 1, wherein the detecting comprises optically detecting by an optical detector.

14. The method of claim 1, wherein the detecting comprises detecting target individual moieties of the long chain target molecules.

15. The method of claim 1, wherein the nanochannel is formed by stacking a plurality of nanoparticles on each other.

16. The method of claim 1, wherein the Raman scattering comprises surface-enhanced coherent anti-Stokes Raman scattering (SECARS) or surface enhanced Raman scattering (SERS).

* * * * *